United States Patent
Puckette

(10) Patent No.: US 11,191,824 B1
(45) Date of Patent: Dec. 7, 2021

(54) METHOD OF PURIFYING VIRUS-LIKE-PARTICLES

(71) Applicant: The Government of the United States of America, as represented by the Secretary of Homeland Security, Washington, DC (US)

(72) Inventor: Michael Puckette, Waterford, CT (US)

(73) Assignee: The Government of the United States of America, as represented by the Secretary of Homeland Security, Washington, DC (US)

(*) Notice: Subject to any disclaimer, the term of this patent is extended or adjusted under 35 U.S.C. 154(b) by 0 days.

(21) Appl. No.: 17/326,023

(22) Filed: May 20, 2021

Related U.S. Application Data

(60) Provisional application No. 63/028,694, filed on May 22, 2020.

(51) Int. Cl.
| | |
|---|---|
| *A61K 39/135* | (2006.01) |
| *A61P 31/14* | (2006.01) |
| *A61K 39/39* | (2006.01) |
| *C12N 7/00* | (2006.01) |
| *A61K 39/00* | (2006.01) |

(52) U.S. Cl.
CPC ............ *A61K 39/135* (2013.01); *A61K 39/39* (2013.01); *A61P 31/14* (2018.01); *C12N 7/00* (2013.01); *A61K 2039/5258* (2013.01); *A61K 2039/552* (2013.01); *C12N 2770/32123* (2013.01); *C12N 2770/32134* (2013.01); *C12N 2770/32151* (2013.01); *C12N 2770/32171* (2013.01)

(58) Field of Classification Search
None
See application file for complete search history.

(56) References Cited

U.S. PATENT DOCUMENTS

| | | | |
|---|---|---|---|
| 9,975,926 B2 | 5/2018 | Puckette et al. | |
| 10,308,927 B2 | 6/2019 | Puckette et al. | |
| 10,385,319 B2 | 8/2019 | Puckette et al. | |
| 10,513,542 B2 | 12/2019 | Puckette et al. | |
| 10,604,548 B2 | 3/2020 | Puckette et al. | |
| 2006/0257852 A1* | 11/2006 | Rappuoli | A61K 39/12 435/5 |
| 2013/0273109 A1* | 10/2013 | Settembre | A61P 15/00 424/233.1 |

OTHER PUBLICATIONS

Miura et al. (Applied and Environmental Microbiology. 2011; 77 (12): 3975-3981).*

* cited by examiner

*Primary Examiner* — Shanon A. Foley
(74) *Attorney, Agent, or Firm* — Lavanya Ratnam; Kelly G. Hyndman; Robert W. Busby

(57) ABSTRACT

A method of producing purified FMDV VLPs, comprising contacting cells containing FMDV VLPs with a lysis buffer and allowing the cells to lyse, the lysis buffer comprising 10-20 mM Tris-HCl, 150-200 mM NaCl, 3 mM $MgCl_2$, and 1% Triton X-100, wherein the lysis buffer does not contain EDTA; centrifuging a solution; and removing a supernatant from the solution, the supernatant containing the purified FMDV VLPs.

20 Claims, 8 Drawing Sheets

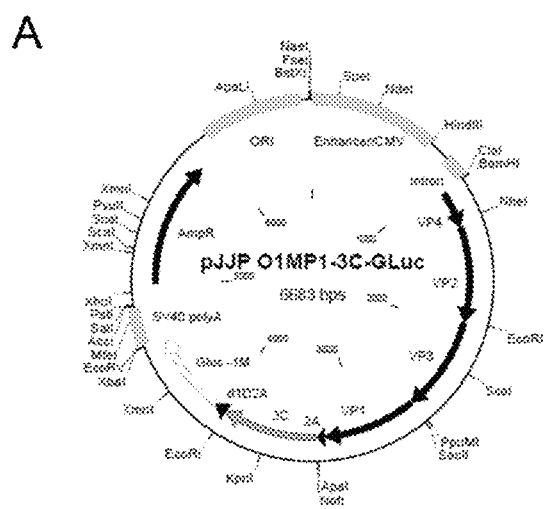
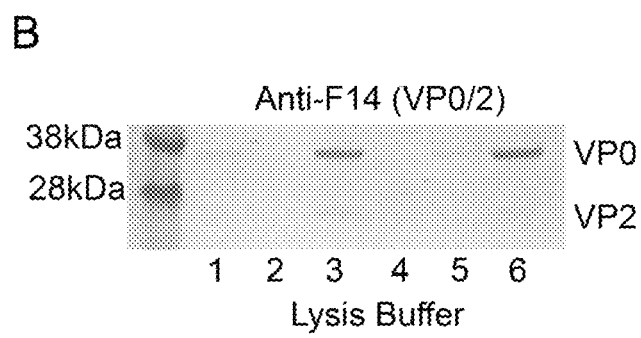
Figure 1A
Figure 1B

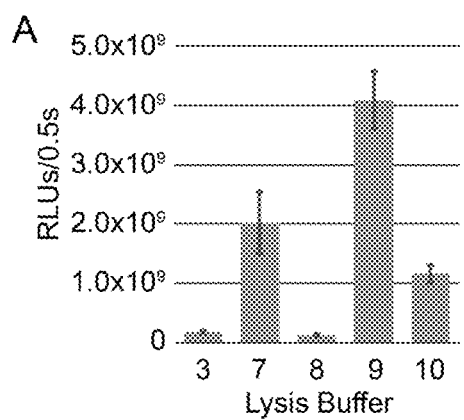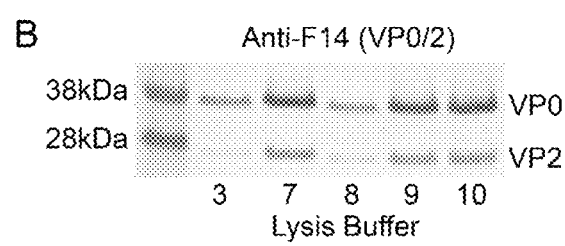
Figure 2A                                   Figure 2B

Figure 5

METHOD OF PURIFYING VIRUS-LIKE-PARTICLES

CROSS REFERENCE TO RELATED APPLICATION

This U.S. Non-provisional application claims the benefit of priority to U.S. Provisional Application No. 63/028,694 filed on May 22, 2020, the disclosures of all of which are herein incorporated by reference in their entirety.

GOVERNMENT RIGHTS

This invention was made with government support awarded by the U.S. Department of Homeland Security. The United States Government has certain rights in this invention.

TECHNICAL FIELD

The present disclosure relates to a method of purifying virus-like-particles (VLPs), such as VLPs from foot-and-mouth disease virus (FMDV). The method produces an increased amount of purified VLPs, and at a lower cost, than that obtained by previous methods. The present disclosure also relates to a method of inoculating an animal with the purified VLPs to induce an immune response to FMDV, and to formulations of the purified VLPs such as in a vaccine.

BACKGROUND

The "background" description provided herein is for the purpose of generally presenting the context of the disclosure. This background is not expressly or impliedly admitted as prior art against the present disclosure.

The foot-and-mouth disease virus (FMDV) is the causative agent of a highly infectious and sometimes fatal disease that affects cloven-hoofed animals such as cattle, pigs, sheep, goats, and deer. There are seven major antigenically distinct FMDV serotypes (A, O, C, Asia 1, SAT 1, SAT 2, and SAT 3), and each serotype contains multiple subtypes or topotypes. Currently, serotype O is the most common serotype worldwide. Example FMDV strains include A24 Cruzeiro, A2006 Turkey, O1 Campos, O1 Manisa, O Pan Asia II, O Hong Kong, C3 Indaial, Asia 1 Shamir, SAT1 KNP91, SAT3 ZIM91, and SAT2 Egypt 2010.

Foot-and-mouth disease outbreaks cause significant agro-economic losses with severe implications for animal farming throughout the world. FMDV can be spread to uninfected livestock by direct contact, through aerosols from infected domestic or wild animals, or through contamination of feed and/or equipment. Containment of an FMDV outbreak demands considerable effort and expenses for vaccination, vigilant and strict monitoring of livestock, and culling and disposal of infected livestock.

Commonly used foot-and-mouth disease vaccines utilize whole virus that has been chemically inactivated. This vaccine platform has several limitations and shortcomings. Animals immunized with inactivated virus are difficult to distinguish from naturally infected animals. The efficacy of the vaccine formulations is limited by immunogenic instability and short vaccine shelf life that results in a loss of potency upon transportation or storage and subsequent induction of insufficient immunity or immunity of a short duration. Furthermore, the set-up and running costs of producing the FMDV vaccine in potent form and securing and maintaining its production facilities are very high.

Newer generations of vaccines utilize FMDV polypeptides expressed from non-infectious vectors, such as a plasmid, to produce immunogenic FMDV antigens. These platforms utilize expression of the FMDV 3C protease to process and cleave the expressed FMDV P1 precursor polypeptide into the virus structural proteins VP0, VP3, and VP4. The fusion protein VP0 is a combination of the structural proteins VP4 and VP2, the processing of VP0 into VP4 and VP2 is not performed by the 3C protease and occurs by an unknown mechanism during encapsulation. The fully processed structural proteins VP4, VP2, VP3, and VP1, can form virus-like-particles (VLPs) for use in vaccines, VP0 can also be incorporated into VLPs in place of VP4 and VP2 VLPs structurally resemble viruses but are non-infectious because they do not contain any viral genetic material. For the purpose of producing a vaccine, extracted antigen is considered a VLP if it elicits a protective immune response against virus challenge in the target species. Additional details of technology related to these VLP vaccines are described in U.S. Pat. Nos. 9,975,926; 10,513,542; 10,604,548; 10,385,319; and 10,308,927, each of which is incorporated by reference in its entirety.

BRIEF SUMMARY

According to a first aspect, the present disclosure provides a method of producing purified VLPs that includes contacting cells containing VLPs with a lysis buffer containing Tris-HCl, NaCl, $MgCl_2$, and Triton X-100, and allowing the cells to lyse. In various embodiments, the lysis buffer does not contain any EDTA. After the cells have lysed, the method further includes centrifuging a solution of the lysed cells and removing the supernatant from the centrifuged solution. The supernatant contains purified VLPs According to various embodiments of the method, the VLPs are FMDV VLPs, and the embodiments are directed to a method of producing purified FMDV VLPs.

According to various embodiments of the method of producing purified VLPs, the lysis buffer contains 20 mM Tris-HCl, 150-200 mM NaCl, 3 mM $MgCl_2$, and 1% Triton X-100 (w/v).

According to some embodiments, the method of producing purified VLPs also includes centrifuging the supernatant through a centrifugal filter with a 1,000,000 Da cut off.

According to some embodiments, the method of producing purified VLPs also includes centrifuging the supernatant through a cesium chloride and/or a sucrose gradient and collecting purified VLPs from the gradient.

In a second aspect, the present disclosure provides a method of inoculating an animal to induce an immune response against FMDV. The method of inoculating includes (i) providing purified FMDV VLPs that have been produced by a method that includes contacting cells containing FMDV VLPs with a lysis buffer that contains Tris-HCl, NaCl, $MgCl_2$, and Triton X-100, centrifuging a solution of the lysed cells, and removing the supernatant containing the purified FMDV VLPs; and (ii) inoculating the animal with an effective amount of the purified FMDV VLPs.

In a third aspect, the present disclosure provides a composition containing purified FMDV VLPs produced by a method that includes contacting cells containing FMDV VLPs with a lysis buffer that contains Tris-HCl, NaCl, $MgCl_2$, and Triton X-100; centrifuging a solution of the lysed cells; and removing the supernatant containing the purified FMDV VLPs.

According to various embodiments, the composition containing FMDV VLPs is a vaccine for foot-and-mouth disease containing an effective amount of the purified FMDV VLPs.

BRIEF DESCRIPTION OF THE DRAWINGS

An appreciation of the disclosure and many of the attendant advantages thereof may be understood by reference to the accompanying drawings. Included in the drawings are the following figures:

FIG. 1A is a plasmid map of the plasmid pJJP O1M-3C (L127P)-GLuc, that was used to produce VLPs in transfected cells. FIG. 1B is a Western blot using F14 antibody for the detection of VP0 and VP2 proteins from supernatants extracted with lysis buffers LB1 through LB6.

FIG. 2A shows the results of luciferase detected in relative luciferase units per half second of supernatant extracted with lysis buffers LB3, LB7, LB8, LB9, and LB10. FIG. 2B is a western blot using F14 antibody for the detection of VP0 and VP2 proteins from supernatants extracted with lysis buffers LB3, LB7, LB8, LB9, and LB10.

FIG. 5 shows cesium chloride gradients on samples extracted using lysis buffer LB9 from HEK293-T cells producing VLPs from different FMDV serotypes and strains. A2006=A2006 Turkey; A24=A24 Cruzeiro; Asia1=Asia 1 Shamir; SAT2=SAT2 Egypt 2010; OIC=O1 Campos; OPA2=O Pan Asia II; OHK=O Hong Kong.

DETAILED DESCRIPTION

Figure 3:
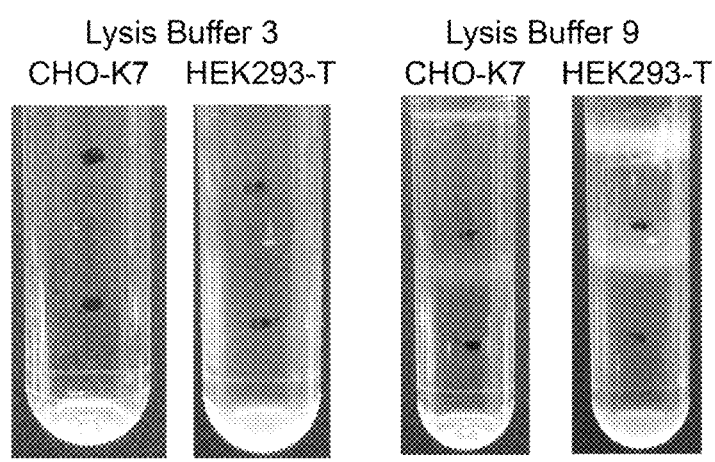
FIG. 3 shows the resulting band patterns observed after size-based purification by cesium chloride gradient of VLPs extracted from CHO-K7 and HEK293-T cells using lysis buffer LB3 or LB9. Banding and material between the black marks represent antigen and the appropriate size range for FMDV VLPs.

In addition to its other benefits, the present disclosure provides a new and advantageous method to produce purified VLPs. In a first aspect, the method utilizes a lysis buffer that results in an increased amount of purified VLPs, and at a much lower cost, than that obtained by previous methods.

For purposes of the present invention, "foot-and-mouth disease virus" or the acronym FMDV refers to any of the seven major FMDV antigenically distinct virus serotypes, i.e. A, O, C, Asia 1 and South African Territories 1, 2 and 3, as well as the multiple subtypes or topotypes that exist within each serotype. In some embodiments, the VLPs are from one or more of FMDV strains A24 Cruzeiro, A2006 Turkey, O1 Campos, O1 Manisa, O Pan Asia II, O Hong Kong, C3 Indaial, Asia 1 Shamir, SAT1 KNP91, SAT3 ZIM91, and SAT2 Egypt 2010. Infection with any one serotype does not confer protective immunity against another.

The FMDV is a non-enveloped picornavirus (belonging to the genus Aphthovirus of the family Picornaviridae) with a single-stranded genomic RNA of between 7,500 to 8,000 nucleotides. The capsid, which is the protein shell of the virus, is made up of 60 copies of each of the four structural proteins VP1, VP2, VP3 and VP4. The precursor protein VP0, a fusion of VP2 and VP4, can also be incorporated into the capsid. In embodiments, during assembly, P1, a 95-kDa capsid polyprotein precursor is cleaved by the viral 3C protease to ultimately yield VP1, VP2, VP3 and VP4.

FMDV P1 precursor polypeptide (or P1 precursor protein) is a polypeptide comprised of the FMDV structural proteins and/or precursors, VP0, VP1, VP2, VP3, and VP4, as well as the 2A translational interrupter. The FMDV P1 precursor is around 85 kDa in molecular weight. The P1 precursor is processed by the FMDV 3C protease into structural proteins forming VLPs and the FMDV capsid.

The FMDV VP0 protein is a precursor peptide comprised of the FMDV VP2 and VP4 structural proteins. The FMDV VP0 protein is also identified as the FMDV 1AB protein and is around 33 kDa in molecular weight. It is produced by the processing of the FMDV P1 precursor protein by the FMDV 3C protease. The FMDV VP0 protein is important in the formation of protomers along with FMDV proteins VP3 and VP1. Five of these protomers assemble into a pentamer and twelve pentamers can assemble into a FMDV capsid or VLP. Cleavage of VP0 into VP2 and VP4 occurs through an unknown mechanism.

The FMDV VP1 protein is a structural protein that comprises the FMDV capsid and/or FMDV VLP. The FMDV VP1 protein is also identified as the FMDV 1D protein and is around 24 kDa in molecular weight. The FMDV VP1 protein contains a mobile loop structure, identified as the G-H loop, which emerges from the surface of the FMDV capsid and/or VLP. The FMDV VP1 protein can form a protomer along with VP0 and VP3. Five of these protomers assemble into a pentamer and twelve pentamers can assemble into a FMDV capsid or VLP.

The FMDV VP2 protein is a structural protein that comprises the FMDV capsid and/or FMDV VLP. The FMDV VP2 protein is also identified as the FMDV 1B protein and is around 24 kDa in molecular weight. The FMDV VP2 protein, along with the FMDV VP4 protein, is part of the FMDV VP0 protein until the formation of FMDV capsids and/or VLPs at which point the VP0 protein is processed into VP2 and VP4.

The FMDV VP3 protein is a structural protein that comprises the FMDV capsid and/or FMDV VLP. The FMDV VP3 protein is also identified as the FMDV 1C protein and is around 24 kDa in molecular weight. The FMDV VP3 protein can form a protomer along with VP0 and VP1. Five of these protomers assemble into a pentamer and twelve pentamers can assemble into a FMDV capsid or VLP.

The FMDV VP4 protein is the smallest of the FMDV structural proteins and is part of the FMDV capsid and/or FMDV VLP. The FMDV VP4 protein is also identified as the FMDV 1D protein and is around 9 kDa in molecular weight. The FMDV VP4 protein, along with the FMDV VP2 protein, is part of the FMDV VP0 protein until the formation of FMDV capsids and/or VLPs at which point the VP0 protein is processed into VP2 and VP4. Unlike other FMDV proteins that comprise the capsid and/or VLP the VP4 protein is entirely located inside the capsid and/or VLP structure.

"Virus-like particles" or "VLPs" resemble viruses, but are non-infectious because they do not contain any viral genetic material. The expression of viral structural proteins, such as envelope or capsid, can result in the self-assembly of VLPs that can stimulate an immune response in a mammalian organism. In other words, VLPs are often empty viral envelopes or empty viral capsids that are capable of stimulating an immune response like a full virus. Methods and problems associated with the production of VLPs in alternative systems include those described by Lee, et al., J. Biomed. Sci. 16:69 (Aug. 11, 2009), Srinivas, et al., Biologicals 44:64-68 (2016), Mayr, et al., Vaccine 19: 2152-2162 (2001) and Niborski, et al., Vaccine 24: 7204-7213 (2006) that are each incorporated by reference.

According to various embodiments of the method, the lysis buffer contains Tris-HCl, NaCl, and Triton X-100. Tris is short for tris(hydroxymethyl)aminomethane. The useful buffer range for tris (7-9) coincides with the physiological pH typical of most living organisms. This, and its low cost, make tris one of the most commonly used buffers. NaCl to help keep proteins soluble and to mimic physiological conditions. NaCl can also be used to lyse cells through osmosis. Triton X-100 is a nonionic surfactant that has a hydrophilic polyethylene oxide chain (on average it has 9.5 ethylene oxide units) and an aromatic hydrocarbon lipophilic or hydrophobic group Triton X-100 is a commonly used detergent in laboratories. Triton X-100 is widely used to lyse cells to extract protein or organelles, or to permeabilize the membranes of living cells.

In some embodiments, the lysis buffer does not contain ethylenediaminetetraacetic acid (EDTA). In some embodiments, the lysis buffer further contains $MgCl_2$. In some embodiments, the lysis buffer contains 10-20 mM Tris-HCl, 150-200 mM NaCl, and 1% Triton X-100 (w/v).

In some embodiments, the lysis buffer contains 10-20 mM Tris-HCl, 150-200 mM NaCl, 3 mM $MgCl_2$, and 1% Triton X-100 (w/v). In an embodiment, the lysis buffer contains 20 mM Tris-HCl, 200 mM NaCl, 3 mM $MgCl_2$, and 1% Triton X-100 (w/v) and does not contain EDTA.

In embodiments of the method, cells containing VLPs are contacted with the lysis buffer and the cells allowed to lyse. A solution of the lysed cells is then centrifuged to pellet the cellular components, while the VLPs remain in the supernatant. The supernatant containing the VLPs is then removed.

According to various embodiments, the method of purifying VLPs further includes centrifuging the supernatant through a gradient, such as a cesium chloride gradient, a sucrose gradient, or both.

According to various embodiments, the cells containing the VLPs are eukaryotic cells. In some embodiments, the cells are mammalian cells. In some embodiments, the cells are insect cells. In further embodiments, the cells are CHO-K7 or HEK293-T cells.

According to various embodiments of the method, the purified VLPs are immunogenic and capable of inducing an immune response when an effective amount is inoculated in animals. In embodiments, the purified VLPs are capable of eliciting protection from foot-and-mouth disease (FMD) in the inoculated animal.

In a second aspect, the present disclosure provides a method of inoculating an animal to induce an immune response against FMDV. In embodiments, the method induces an immune response that protects the animal from FMDV.

The method of inoculating includes (i) providing FMDV VLPs that have been purified by a method that includes contacting cells containing FMDV VLPs with a lysis buffer that contains Tris-HCl, NaCl, and Triton X-100, centrifuging a solution of the lysed cells, and removing the supernatant containing the purified FMDV VLPs; and (ii) inoculating the animal with an effective amount of the purified FMDV VLPs.

According to various embodiments, the lysis buffer does not contain EDTA. In some embodiments, the lysis buffer further contains $MgCl_2$. In some embodiments, the lysis buffer contains 10-20 mM Tris-HCl, 150-200 mM NaCl, and 1% Triton X-100 (w/v). In some embodiments, the lysis buffer contains 10-20 mM Tris-HCl, 150-200 mM NaCl, 3 mM $MgCl_2$, and 1% Triton X-100 (w/v). In an embodiment, the lysis buffer contains 20 mM Tris-HCl, 200 mM NaCl, 3 mM $MgCl_2$, and 1% Triton X-100 (w/v) and does not contain EDTA.

According to various embodiments, the FMDV VLPs are from one or more of FMDV serotypes A, O, C, Asia, SAT1, SAT2, and SAT 3. In some embodiments, the VLPs are from one or more of FMDV strains A24 Cruzeiro, A2006 Turkey, O1 Campos, O1 Manisa, O Pan Asia II, O Hong Kong, C3 Indaial, Asia 1 Shamir, SAT1 KNP91, SAT3 ZIM91, and SAT2 Egypt 2010. According to various embodiments, the animal is a mammal. In some embodiments, the animal is a goat, a sheep, a pig, or a cow.

According to various embodiments of the method of inoculating an animal, the immune response to FMDV is effective to provide protection against challenge with FMDV. In some embodiments, the effective amount of the FMDV VLPs is an amount effective to produce an immune response that protects the animal against challenge with FMDV. In some embodiments, the animal is inoculated with a vaccine containing an effective amount of the FMDV VLPs.

A vaccine in accordance with the present disclosure is a biological composition that provides or improves immunity to an organism to a particular disease. A vaccine may contain an agent, such as a killed, inactivated, weakened or attenuated form of the disease-causing micro-organism (e.g., virus, bacteria, fungi, algae), its toxins, surface proteins or recombinant nucleic acid such as DNA, compositions or particles that resemble the pathogenic microorganism (e.g., virus-like particles) or combinations thereof. The agent functions as an antigen and is administered to an organism to stimulate the body's immune system to produce an immune response, that may include recognizing the agent as foreign, destroying the agent (e.g., with antibodies produced that are specific to the agent/antigen), and remembering the agent, so the immune system can more easily recognize and destroy any of these microorganisms that it later encounters, for example, an infection.

Virus-like particles, or VLPs, can be used in accordance with embodiments of the present disclosure. VLPs are recombinant particles with viral matrix or structural proteins such as capsids that resemble viruses, but are non-infectious and unable to propagate as they, respectively, do not contain any viral genetic material. VLPs can be utilized as vaccine antigens as they mimic the native virions, and can be produced in vitro in a variety of cell culture systems including mammalian cell lines, insect cell lines, yeast and plant cells or in vivo. In embodiments, FMDV VLPs consist essentially of assembled structural proteins or assembled capsid proteins (e.g., VP1, VP2, VP3 and VP4).

In a third aspect, the present disclosure provides a composition containing VLPs purified by a method that includes contacting cells containing VLPs with a lysis buffer that contains Tris-HCl, NaCl, and Triton X-100; centrifuging a solution of the lysed cells; and removing the supernatant containing the purified VLPs. According to various embodiments, the VLPs are FMDV VLPs.

In some embodiments, the lysis buffer consists of 10-20 mM Tris-HCl, 150-200 mM NaCl, and 1% Triton X-100 (w/v). In some embodiments, the lysis buffer consists of 10-20 mM Tris-HCl, 150-200 mM NaCl, 3 mM $MgCl_2$, and 1% Triton X-100 (w/v).

In various embodiments, the FMDV VLPs are from one or more of FMDV serotypes A, O, C, Asia, SAT1, SAT2, and SAT 3. In some embodiments, the VLPs are from one or more of FMDV strains A24 Cruzeiro, A2006 Turkey, O1 Campos, O1 Manisa, O Pan Asia II, O Hong Kong, C3 Indaial, Asia 1 Shamir, SAT1 KNP91, SAT3 ZIM91, and SAT2 Egypt 2010.

According to various embodiments, the composition is a vaccine for FMD containing an effective amount of FMDV VLPs. In some embodiments, the vaccine further comprises an adjuvant.

EXPERIMENTAL DATA

Example 1 Buffer Comparisons

An initial selection of six lysis buffers was evaluated in a method for preparing VLP's. The buffers included four lysis buffers, LB1-LB4, that were selected from an internet and literature search of buffers used with cytosolic viruses, specifically Herpesviruses. Two commercially produced buffers, LB5 and LB6, were also included in the testing to serve as benchmarks by which other lysis buffers could be compared. LB5 is M-PER™ buffer available from Thermo Scientific and contains a proprietary detergent in 25 mM bicine buffer (pH 7.6) (M-PER Mammalian Protein Extraction Reagent User Manual, Thermo Scientific). LB6 is XTRACTOR™ buffer available from Clontech Laboratories and is based on a mild non-ionic detergent (xTractor Buffer & xTractor Buffer Kit User Manual, Clontech Laboratories).

The components of the lysis buffers are shown in Table 1. The exact components of the commercial buffers LB5 and LB6 are not publicly known.

fications include the utilization of polyethylenimine, MW 25000, as a transfection reagent instead of LIPO-FECTAMINE™ 2000. Transfection of cell cultures utilized the pJJP O1M-3C(L127P)-GLuc plasmid, FIG. 1A. In addition to the FMDV P1-2A and 3C protease coding sequences this plasmid contains the sequence to *Gaussia* luciferase, which can be measured using a luciferase assay to quickly quantify differences in protein concentrations. The results of lysis of transfected cells with LB1, LB2, LB3, LB4, LB5, and LB6 are shown in FIG. 1B. Of tested, LB3 performed the best of the non-commercial buffers. Buffers containing EDTA underperformed (LB1, LB2, and LB4).

Based on initial results of underperformance of EDTA containing buffers, four additional lysis buffers were formulated. These buffers are identified as LB7 through LB10 and were compared to LB3 to determine if further enhancement in VLP extraction could be obtained by the addition of Triton X-100, addition of $MgCl_2$, and/or an increase in the amount of NaCl (Table 1). Cell supernatants were evaluated for their luciferase activity, FIG. 2A, and by Western blot with the F14 antibody, FIG. 2B.

As shown by the results in FIGS. 2A and 2B, lysis buffers LB7, LB9, and LB10 showed improvement over LB3, with LB9 being the top performer.

Example 2 Luciferase Assay

Luciferase assay was performed by removal of cells from flasks and centrifugation at 500×g for 10 minutes. Media was removed and cells washed twice with 5 mL of DPBS to ensure the removal of any residual media. Cell pellets were resuspended in 2 mL of each tested lysis buffer separately and allowed to incubate on a rocker for 10 minutes to induce cell lysis. Luciferase assay was performed using LUMI-TRAC white 96 well plates (Greiner) in a 96-well BioSystems Veritas luminometer (Turner Biosystems) with a mixture of 10 ul of cell lysis mixed with 90 ul of ddH2O in triplicate wells for samples. An injection of 100 ul of 50 ug/mL of water-soluble coelentrazine (NanoLight Technologies) with an integration time of 0.5 seconds before and after injection of substrate. Data was recorded in the form of relative luciferase units (RLUs) per half second.

Example 3 Additional Purification—$CsCl_2$ Gradient

Subsequent experiments used both LB3 and LB9 to extract VLPs of FMDV strain O1 Manisa from CHO-K7 and

TABLE 1

| ID | Source | Components |
|---|---|---|
| LB1 | Internet Search | 10 mM Tris-HCl, 200 mM NaCl, 10 mM EDTA, 1% Triton X-100 |
| LB2 | Internet Search | 50 mM Tris-HCl, 150 mM NaCl, 10 mM EDTA, 1% Triton X-100 |
| LB3 | Internet Search | 20 mM Tris-HCl, 150 mM NaCl, 3 mM MgCl2 |
| LB4 | Internet Search | 20 mM Tris-HCl, 150 mM NaCl, 3 mM MgCl2, 10 mM EDTA |
| LB5 | Commercial, MPER buffer | |
| LB6 | Commercial, Xtractor buffer | |
| LB7 | Derived from LB 3 | 20 mM Tris-HCl, 150 mM NaCl, 3 mM MgCl2, 1% Triton X-100 |
| LB8 | Derived from LB 3 | 20 mM Tris-HCl, 200 mM NaCl, 3 mM MgCl2 |
| LB9 | Derived from LB 3 | 20 mM Tris-HCl, 200 mM NaCl, 3 mM MgCl2, 1% Triton X-100 |
| LB10 | Derived from LB1 | 10 mM Tris-HCl, 200 mM NaCl, 1% Triton X-100 |

The lysis buffers were evaluated by western blot with the extracted supernatant and the F14 antibody, which detects FMDV VP0 and VP2. Transfected mammalian cell cultures were used to produce VLPs in a similar means as in U.S. Pat. No. 10,385,319, the contents of which is incorporated by reference in its entirety, with some modifications. The modifications include HEK293-T cells for comparison by cesium chloride gradient. Cell lysis products were layered on 2 mL cesium chloride 2-step discontinuous gradients (1.42 g/cm³/1.38 g/cm3) prepared in TEN buffer (0.05M Tris, 0.001 M EDTA, 0.15 M NaCl, pH 7.4). Samples were centrifuged in a SW40Ti rotor at 217,485×g for 18 hours using an Optima L-80 XP ultracentrifuge (Beckman Coulter). Individual visible bands were collected and dialyzed against PBS at 4° C. using 10K MWCO Slide-A-Lyzer Dialysis Cassettes (Thermo Fisher Scientific). Post-dialysis samples were run on western blots and analyzed with monoclonal antibody F1412SA.

Cesium chloride gradients are shown in FIG. 3. The material banding between the black marks represents VLPs at the appropriate size range for FMDV VLPs. In this test, LB9 continued to outperform LB3.

Figures 4A, 4B:
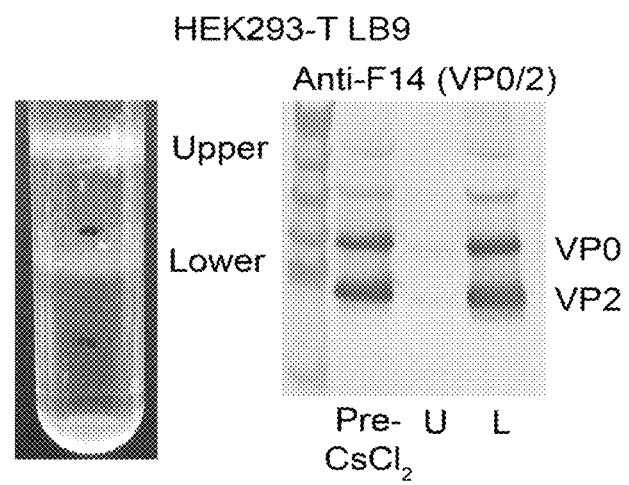
FIG. 4A shows the band pattern from a cesium chloride gradient purification of VLPs extracted from HEK393-T cells using lysis buffer LB9.
FIG. 4B Upper (U) and lower (L) bands were extracted and run on a Western blot, alongside an aliquot that was not applied to a cesium chloride gradient (Pre $CsCl_2$), using the F14 antibody for detection of FMDV proteins VP0 and VP2.

The VLP Bands were extracted and dialyzed into phosphate buffered saline, and then used for Western blot analysis with F14 antibody. The results are shown in FIGS. 4A and 4B.

Vaccines using VLPs extracted with LB9 and VLPs extracted by a previous method (Qproteome Cell Compartment Kit, Qiagen) were compared in a swine challenge study with FMDV O1 Manisa. The results presented in Table 2 show that LB9 extracted VLPs protected five of five swine from O1 Manisa challenge, while the Qproteome lysis buffer protected four of five from challenge. This study demonstrates that utilization of LB9 to extract antigen does not render the vaccine non-functional. While the sample number in this study is limited, the LB9 extracted VLPs may produce a superior result than the previous Qproteome method (5/5 compared to 4/5).

TABLE 2

|  | Animal No./ Gender | VNT 0 dpcc | 3 dpcc | 6 dpcc | 8 dpcc | 10 dpcc | 14 dpcc | Conclusion |
|---|---|---|---|---|---|---|---|---|
| Qproteome Lysis Buffer extracted VLPS | 51824 M | 2.4 | NEG | NEG | NEG | NEG | POS(2) | Unprotected |
|  | 51830 F | 1.8 | NEG | NEG | NEG | NEG | NEG | Protected |
|  | 51837 F | 2.1 | NEG | NEG | NEG | NEG | NEG | Protected |
|  | 51839 M | 0.9 | NEG | NEG | NEG | NEG | NEG | Protected |
|  | 51840 M | 1.5 | NEG | NEG | NEG | NEG | NEG | Protected |
| Lysis Buffer 9 Extracted VLPs | 51826 M | 2.1 | NEG | NEG | NEG | NEG | NEG | Protected |
|  | 51829 M | 0.9 | NEG | NEG | NEG | NEG | NEC | Protected |
|  | 55833 F | 1.2 | NEG | NEG | NEG | NEG | NEG | Protected |
|  | 51836 F | 2.1 | NEG | NEG | NEG | NEG | NEG | Protected |
|  | 51841 M | 1.2 | NEG | NEG | NEG | NEG | NEG | Protected |

FIG. 4A is a cesium chloride gradient of VLPs extracted from HEK293-T cells using lysis buffer LB9. In FIG. 4B, Upper (U) and Lower (L) bands were extracted and run on the Western blot, along with an aliquot of VLP supernatant that was not applied to a cesium chloride gradient (Pre-CsCl$_2$), using the F14 antibody for detection of the FMDV VP0 and VP2 proteins.

Figure 5:
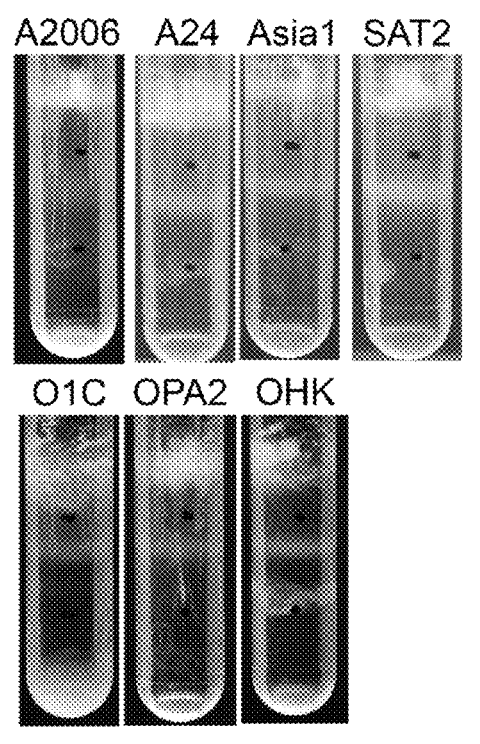

Lysis buffer LB9 was tested for the ability to extract VLPs from several different FMDV strains representative of four different serotypes, A, Asia, O, and SAT2. FIG. 5 shows cesium chloride gradients of the VLPs extracted from HEK293-T cells using LB9. The hazy material banding between the black marks on the tubes are VLPs, that are at the appropriate size range for FMDV VLPs. By this analysis, LB9 is capable of purifying VLPS from each strain and serotype tested.

Figure 6:
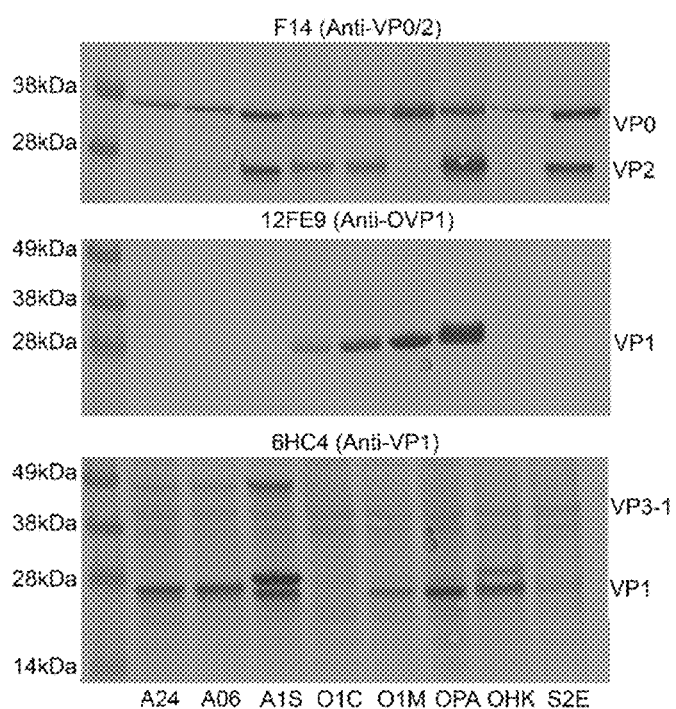
FIG. 6 shows Western blots using F14, 12FE9, and 6HC4 antibodies on samples extracted using lysis buffer LB9 from HEK293-T cells transfected with plasmids encoding different FMDV serotypes and strains. A24=A24 Cruzeiro; A06=A2006 Turkey; A1S=Asia 1 Shamir; O1C=O1 Campos; O1M=O1 Manisa; OPA=O Pan Asia II; OHK=O Hong Kong; SE2=SAT2 Egypt 2010.

Lysis buffer LB9 was tested for the ability to extract antigen from several different FMDV strains/serotypes. Results of the Western blot analyses in FIG. 6 show that LB9 is capable of extracting antigen for each strain and serotype tested.

Example 4 Swine Challenge Study of Vaccines

Animals were vaccinated in a prime/boost format with different dosages of extracted VLPs. Boost vaccination occurred 14 days after the prime vaccination and 7 days prior to challenge. For contact challenge studies in swine, five naïve unvaccinated pigs were infected via intradermal heel bulb (IDHB) inoculation with FMDV O1 Manisa and co-mingled with vaccinated animals, as well as naïve unvaccinated sentinel animals. Animals were inspected for the presence of vesicular lesions at 1, 3, 5, 7, 10, and 14 days post challenge. Animals were considered protected from clinical disease if no lesions were observed for the duration of the study. For all challenge studies, 100% of sentinel animals demonstrated clinical FMDV lesions confirming disease spread.

Usage of LB9 results in a dramatic reduction in potential costs for producing VLPs as LB9 costs roughly $0.005 per dose in reagents, while a commonly used commercial lysis buffer costs about $31.00 per dose (e.g., Qproteome Cell Compartment Kit, Qiagen).

Animals were vaccinated in a prime/boost format with different dosages of either QLB or LB9 derived VLPs are shown in Table 3.

TABLE 3

| Method | n | Dosage (ml) | % Protected |
|---|---|---|---|
| LB9 - VLP | 5 | 0.825 | 100% |
| LB9 - VLP | 5 | 0.6 | 100% |
| QLB - VLP | 5 | 1.4 | 60% |
| QLB - VLP | 5 | 0.75 | 80% |
| QLB - VLP | 5 | 0.35 | 80% |
| QLB - VLP | 5 | 0.0875 | 40% |

Example 5 Determination of Virus Neutralizing Titers (VNTs)

Virus neutralizing antibody titers against FMDV serotype O1 Manisa was determined by VNT on BHK-21 cells as per World Organisation for Animal Health (O1E) protocols. Neutralization titers are expressed as the $\log_{10}$ of the reciprocal of the highest serum dilution resulting in 50% neutralization of the cytopathic effect (Spearman-Kärber method).

VNT by Method

Figure 7:
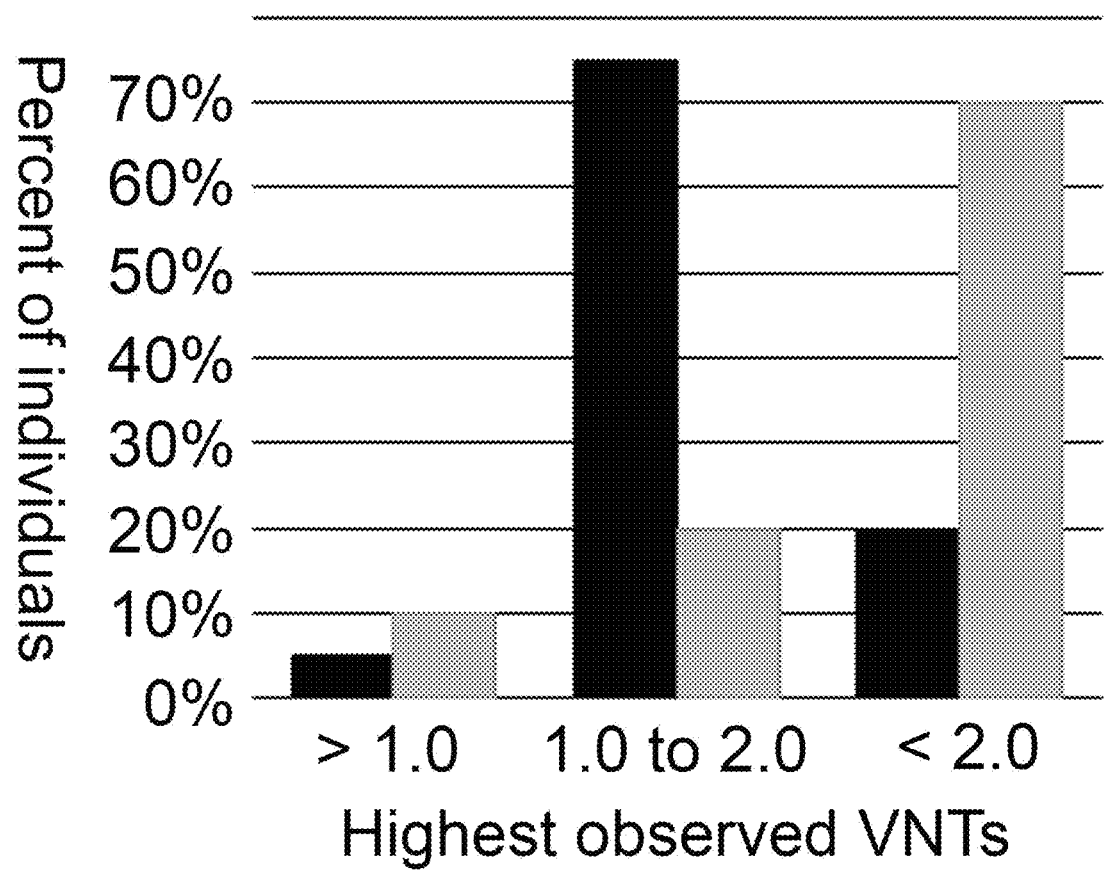
FIG. 7 shows the highest observed VNTs for each pig during the course of the challenge studies sorted in relation to VLPs extracted with either QLB (black) or LB9 (gray).

In FIG. 7, the highest observed VNTs for each pig during the course of the experiment was sorted in relation to VLPs extracted with either QLB (black) or LB9 (gray). This data was sorted into one of three groups, VNTs less than 1.0, VNTs between 1.0 and 2.0, and VNTs above 2.0. For animals vaccinated with LB9, 70% had VNTs above 2.0 at some point during the experiment compared to only 20% of animals vaccinated with QLB. A majority of animals, over 70%, vaccinated with QLB presented with VNTs in the range of 1.0 and 2.0.

VNT by Group

Figure 8:
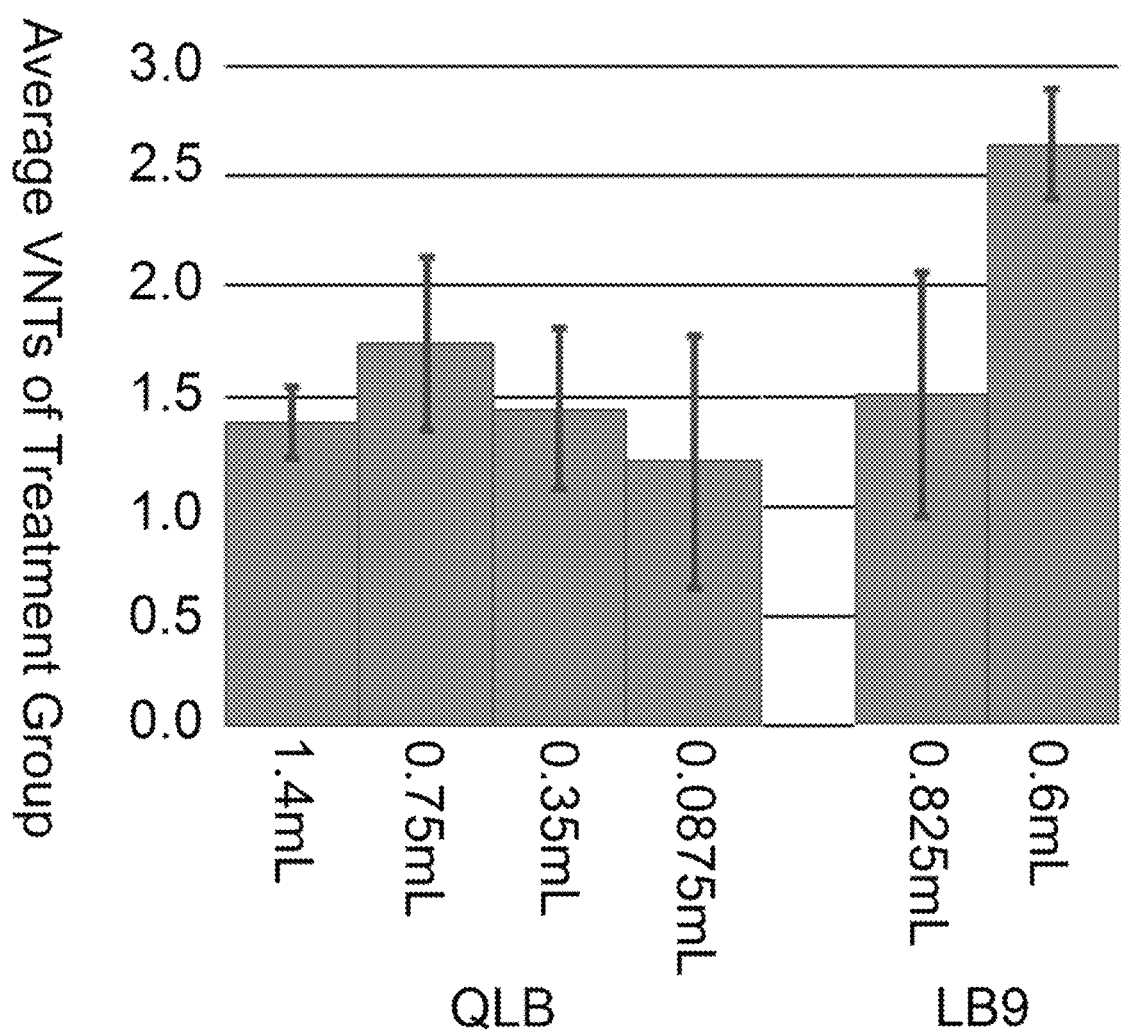
FIG. 8 shows The VNTs at the time of challenge of all animals within a treatment group were averaged together and are presented.

The VNTs at the time of challenge of all animals within a treatment group were averaged together and are presented in FIG. 8. Changes in dosage did not have an effect on the VNTs resulting from VLPs extracted with QLB, while it did have an effect on the VNTs from VLPs extracted with LB9. This suggests that VLPs extracted with QLB and LB9 are stimulating the immune system in different ways.

The foregoing disclosure provides examples of specific embodiments. As will be understood by those skilled in the art, the approaches, methods, techniques, materials, devices, and so forth disclosed herein may be embodied in additional embodiments as understood by those of skill in the art, it is the intention of this application to encompass and include such variations. Accordingly, this disclosure is illustrative and should not be taken as limiting the scope of the following claims.

We claim:

1. A method of producing purified FMDV VLPs, comprising:
    a) contacting cells containing FMDV VLPs with a lysis buffer and allowing the cells to lyse, the lysis buffer comprising:
        10-20 mM Tris-HCl,
        150-200 mM NaCl,
        3 mM $MgCl_2$, and
        1% Triton X-100,
        wherein the lysis buffer does not contain EDTA;
    b) centrifuging a solution of step (a); and
    b) removing a supernatant from the solution of step (b), the supernatant containing the purified FMDV VLPs.

2. The method of claim 1, wherein the FMDV VLPs are chosen from one or more of FMDV serotypes A, O, C, Asia, SAT1, SAT2, and SAT3.

3. The method of claim 1, wherein the FMDV VLPs are chosen from one or more of FMDV strains A24 Cruzeiro, A2006 Turkey, O1 Campos, O1 Manisa, O Pan Asia II, O Hong Kong, C3 Indaial, Asia 1 Shamir, SAT1 KNP91, SAT3 ZIM91, and SAT2 Egypt 2010.

4. The method of claim 1, further comprising centrifuging the supernatant through a cesium chloride and/or sucrose gradient.

5. The method of claim 1, wherein the cells are eukaryotic cells.

6. The method of claim 1, wherein the cells are mammalian cells.

7. The method of claim 1, wherein the cells are insect cells.

8. The method of claim 1, wherein the cells are CHO-K7 or HEK293-T cells.

9. The method of claim 1, wherein the FMDV VLPs are immunogenic and capable of eliciting protection from foot-and-mouth disease (FMD).

10. A method of inoculating an animal to induce an immune response to FMDV, comprising:
    a) providing purified FMDV VLPs produced according to the method of claim 1; and
    b) inoculating the animal with an effective amount of the FMDV VLPs.

11. The method of claim 10, wherein the animal is a mammal.

12. The method of claim 10, wherein the animal is a pig, cow, goat, or sheep.

13. The method of claim 10, wherein the FMDV VLPs are from one or more of FMDV serotypes A, O, C, Asia, SAT1, SAT2, and SAT3.

14. The method of claim 10, wherein the FMDV VLPs are from one or more of FMDV strains A24 Cruzeiro, A2006 Turkey, O1 Campos, O1 Manisa, O Pan Asia II, O Hong Kong, C3 Indaial, Asia 1 Shamir, SAT1 KNP91, SAT3 ZIM91, and SAT2 Egypt 2010.

15. The method of claim 10, wherein the animal is inoculated with a vaccine containing the effective amount of the FMDV VLPs.

16. The method of claim 10, wherein the immune response is effective to provide protection against challenge with FMDV.

17. The method of claim 10, wherein the effective amount of the FMDV VLPs is an amount effective to produce an immune response that protects the animal against challenge with FMDV.

18. A composition comprising purified FMDV VLPs produced by the method according to claim 1.

19. The composition of claim 18, wherein the composition is a vaccine for foot-and-mouth disease comprising an effective amount of the FMDV VLPs.

20. The composition of claim 19, further comprising an adjuvant.

* * * * *